(12) United States Patent
Cho et al.

(10) Patent No.: US 6,905,829 B2
(45) Date of Patent: Jun. 14, 2005

(54) METHOD FOR DETECTING HYBRIDIZED NUCLEIC ACID WITH IMPROVED SENSITIVITY

(75) Inventors: Yoon Kyoung Cho, Kyounggi-do (KR); Hee Kyun Lim, Inchun (KR)

(73) Assignee: Samsung Electronics Co., Ltd., Kyounggi-Do (KR)

( * ) Notice: Subject to any disclaimer, the term of this patent is extended or adjusted under 35 U.S.C. 154(b) by 102 days.

(21) Appl. No.: 10/311,939

(22) PCT Filed: Apr. 17, 2002

(86) PCT No.: PCT/KR02/00705
§ 371 (c)(1),
(2), (4) Date: Dec. 17, 2002

(87) PCT Pub. No.: WO02/083949
PCT Pub. Date: Oct. 24, 2002

(65) Prior Publication Data
US 2003/0198979 A1 Oct. 23, 2003

(51) Int. Cl.$^7$ .................................. C12Q 1/68
(52) U.S. Cl. .......................... 435/6; 196/199
(58) Field of Search .................. 435/6, 196, 199

(56) References Cited

U.S. PATENT DOCUMENTS

| | | |
|---|---|---|
| 4,851,330 A | 7/1989 | Kohne |
| 5,288,611 A | 2/1994 | Kohne |
| 5,567,587 A | 10/1996 | Kohne |
| 5,601,984 A | 2/1997 | Kohne |
| 5,612,183 A | 3/1997 | Kohne |
| 6,043,031 A | 3/2000 | Köster et al. |
| 6,090,933 A | 7/2000 | Kayyem et al. |
| 6,096,273 A | 8/2000 | Kayyem et al. |
| 6,117,631 A | 9/2000 | Nilsen |
| 6,141,096 A | 10/2000 | Stern et al. |
| 2002/0090614 A1 * | 7/2002 | Zhang et al. ............ 435/6 |
| 2003/0138838 A1 * | 7/2003 | Wang et al. ............ 435/6 |

OTHER PUBLICATIONS

Dmitri Proudnikov et al., Immobilization of DNA in Polyacrylamide Gel for the Manufacture of DNA and DNA–Oligonucleotide Microchips, Anal Biochem., 259:31–41 (1998).

Adam B. Steel, et al., Electrochemical Quantitation of DNA Immobilized on Gold, Analytical Chemistry, vol. 70, No. 22, 4670–4677 (1998).

Shana O. Kelly, Photoinduced Electron Transfer in Ethidium–Modified DNA Duplexes: Dependence on Distance and Base Stacking, J. Am. Chem. Soc. 119, 9861–9870 (1997).

Koji Hashimoto, et al., Novel DNA sensor for electrochemical gene detection, Analytica Chimica Acta, 286, 219–224 (1994).

J. Fritz, et al., Translationg Biomolecular Recognition into Nanomechanics, Science Magazine, vol. 288, 316–318 (2000).

Yoshio Okahata, et al., Kinetic Measurements of DNA Hybridization on an Oligonucleotide–Immobilized 27–MHz Quartz Crystal Microbalance, Anal. Chem., 70, 1288–1296 (1998).

Mary E. Napier, et al., Probing Biomolecule Recognition with Electron Transfer: Electrochemical Sensors for DNA Hybridization, American Chemical Society 8, 906–913(1997).

Daniel P. Little, MALDI on a Chip: Analysis of Arrays of Low–Femtomole to Subfemtomole Quantities of Synthetic Oligonucleotides and DNA Diagnostic Products Dispensed by a Piezoelectric Pipet, Anal. Chem. 69, 4540–4546 (1997).

* cited by examiner

Primary Examiner—James S. Ketter
(74) Attorney, Agent, or Firm—Darby & Darby

(57) ABSTRACT

The present invention provides a method for improving detection sensitivity of hybridized nucleic acid immobilized on a solid support of sensing device for gene assay, by removing non-hybridized nucleic acid probe using nuclease from the solid support. In accordance with the invented method, background signal caused by single stranded probe that is not hybridized with target nucleic acid or signal caused by non-specific binding of target nucleic acid to probe is decreased or removed, which improves detection sensitivity of hybridization with a high accuracy, and minimizes the loss of hybridized nucleic acid in the course of washing background signal removed in the conventional method.

6 Claims, 4 Drawing Sheets

METHOD FOR DETECTING HYBRIDIZED NUCLEIC ACID WITH IMPROVED SENSITIVITY

BACKGROUND OF THE INVENTION

1. Field of the Invention

The present invention relates to a method for detecting hybridized nucleic acid with improved sensitivity, more specifically, to a method for improving detection sensitivity for hybridized nucleic acid which is immobilized on a solid support of sensing device for genetic analysis, by removing non-hybridized nucleic acid probe from the solid support with the aid of nuclease.

2. Background of the Invention

Hyperlipidemia is a crucial factor which causes cardiovascular disease with a high death rate. At present, most substances developed as therapeutic agents for hyperlipidemia are inhibitors of HMG-CoA reductase, one of the cholesterol biosynthetic enzymes, and are useful for the treatment of hypercholesterolemia and hyperlipidemia.

The probe-based assay is useful to detect, quantify and analyze nucleic acid. Nucleic acid probe has long been used for sample analysis of bacteria, fungi, virus or other organisms to examine the existence of target nucleic acid (see: U.S. Pat. No. 4,851,330; U.S. Pat. No. 5,288,611; U.S. Pat. No. 5,567,587; U.S. Pat. No. 5,601,984; U.S. Pat. No. 5,612,183). In addition, the probe-based assay is useful to diagnose genetic diseases. Nevertheless, the probe-based assay has not been commercially applied in the art, since it does not meet the requirements of specificity, sensitivity and reliability.

Recently, the sequence analysis of human genome has motivated the development of DNA chip to analyze genome sequence and diagnose disease. DNA chip is prepared by immobilizing single strand DNA probes with previously known sequences on a solid support such as silicon or glass with a high density. Upon reacting unknown sample onto the chip, hybridization occurs between the probe on the chip and its complementary DNA in the unknown sample. By detecting the said hybridization on the chip, nucleic acid sequence in the unknown sample can be determined.

By employing the DNA chip, enormous genetic information can be analyzed in a simple and simultaneous manner and the relationship between the genes can be elucidated, which allows broad applications of the DNA chip in the field of diagnosis of hereditary disease and cancer, investigation of mutants, detection of pathogenic microorganism, analysis of gene expression and development of new drug. In addition, the chip is applicable to almost all bio-industry such as mass production of the antidote by screening genes coding for detoxification material using it as a sensor of microbial or environmental pollution, plant production for medical use and low-fat meat. And then, it can bring about a revolutionary development in the bio-industry.

DNA chip can be classified into two groups, i.e., oligo chip and cDNA chip depending on the kinds of probes thereon, and into photolithography chip, pin-type spotting chip, inkjet-type spotting chip and electronic addressing DNA chip depending on chip fabrication method. Nevertheless, all of the DNA chips until now share common points that various single strand DNA probes are immobilized on a chip and desired information can be obtained by measuring the hybridization degree of target DNA.

Therefore, in order to obtain precise results, it is very important to develop a detection method assuring accurate hybridization signal of the target DNA and the probe DNA on a chip.

The conventional DNA chips detect residual signal on the surface of chip by a confocal microscope or a CCD camera after labeling fluorescence to target DNA and reacting it to the probe on the chip (see: U.S. Pat. No. 6,141,096). In the fluorescent image analysis, various researches for increasing the quantity of fluorescence that can be attached to the chip surface have been made to detect the signal using relatively low-priced CCD-type scanner instead of the conventional expensive confocal-type scanner. For example, many approaches are being performed such as a method employing 3-dimensional hydrogel pad (see: Anal. Biochem., 259:34–41, 1998), a method for increasing density of the probe and fluorescence using dendrimer (see: U.S. Pat. No. 6,117,631) and a method for immobilizing probe onto the porous surface using glass support with a specific pore form (see: Microarray Biochip Technology, pp. 87–117, Edited by Mark Schena, 2000 Bio Techniques Books, Natick, Mass., U.S.A.).

However, the prior optical detection methods have been proven to be less satisfactory in a sense that it is very difficult to detect small quantity of the hybridization signal, to detect the signal accurately due to background noise, to miniaturize and to gain digitalized output. In order to overcome the said shortcomings, many approaches to develop a new detection method in which results are obtained in a form of electric signal instead of optical signal are being performed.

A method for detecting DNA hybridization by the aid of electrochemical technique using conductive metal compound has been reported in the art (see: U.S. Pat. No. 6,096,273; U.S. Pat. No. 6,090,933), where DNA hybridization is detected electrochemically by measuring the redox marker of conductive metal complex upon DNA hybridization (see: Anal. Chem., 70:4670–4677, 1998; J. Am. Chem. Soc., 119:9861–9870, 1997; Analytica Chimica Acta, 286:219–224, 1994; Bioconjugate Chem., 8:906–913, 1997).

In addition, the researches for analyzing the hybridization without fluorescence or any other tagging substance are in active progress. For example, there is a method for measuring the binding capacity between the DNA oligomer probe and target DNA using microfabricated cantilever, by which, a single nucleotide difference can be analyzed (see: Science, 288:316–318, 2000). Besides, a method for measuring the mass difference caused by DNA hybridization using quartz crystal microbalance (see: Anal. Chem., 70:1288–1296, 1998) or using MALDI mass spectrometry (Matrix Assisted Laser Desorption/Ionization mass spectrometry) is under development as well (see: Anal. Chem., 69:4540–4546, 1997; U.S. Pat. No. 6,043,031).

As illustrated above, in all detection methods employed in DNA chips using complementary DNA binding, the detection selectivity for hybridized DNA can be improved by maximizing the difference of pre-hybridization signal and post-hybridization signal. Accordingly, it is expected that decreasing or removing background signals caused by non-hybridized single strand probe or signals caused by non-specific binding of target nucleic acid to probe may improve the detection accuracy and selectivity for the hybridized DNA.

SUMMARY OF THE INVENTION

The present inventors found that the detection sensitivity for hybridization can be improved dramatically, by removing residual non-hybridized single strand nucleic acid probe using nuclease after hybridization.

A primary object of the present invention is, therefore, to provide a method for improving detection sensitivity for the hybridized nucleic acid immobilized on a solid support of sensing device for genetic analysis, by removing non-hybridized nucleic acid probes from the solid support with the aid of nuclease.

BRIEF DESCRIPTION OF THE DRAWINGS

The above and the other objects and features of the present invention will become apparent from the following description given in the conjunction with the accompanying drawings, in which.

DETAILED DESCRIPTION OF THE INVENTION

The present invention provides a method for improving detection sensitivity for the hybridized nucleic acid comprising the steps of immobilizing probes with previously known sequences on a solid support of sensing device for genetic analysis, hybridizing target DNA to a DNA chip, and removing residual single strand DNA probe with the aid of nuclease. The solid support of sensing device for genetic analysis includes a planar, non-porous solid support such as glass, quartz, silicones, plastics, etc.

Figure 1:
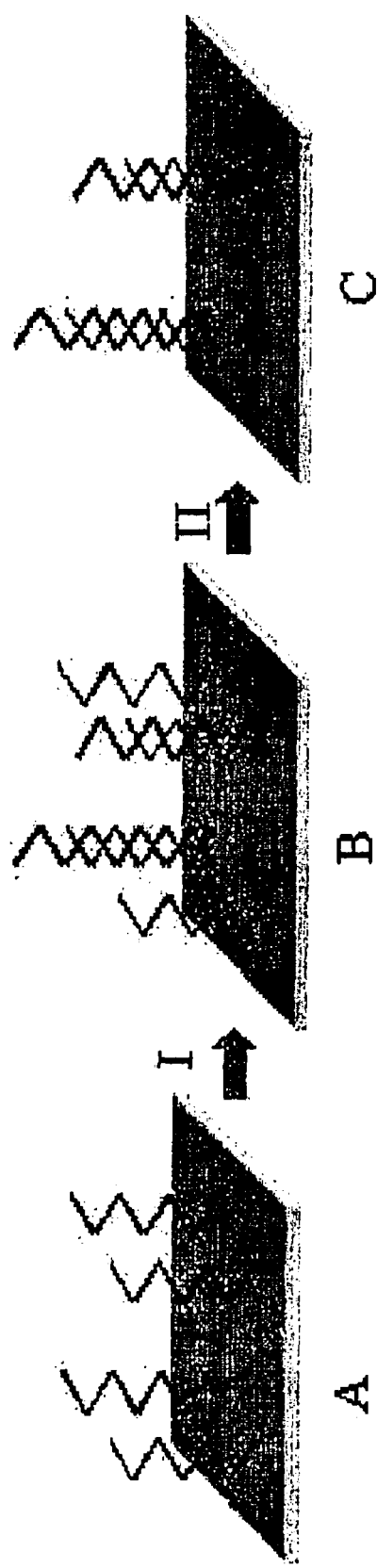
FIG. 1 is a schematic diagram showing the principle of improving detection selectivity for the hybridized nucleic acids with the aid of nuclease.

FIG. 1 is a schematic diagram showing the principle of improving detection selectivity for the hybridized nucleic acid with the aid of nuclease, where (A), (B) and (C) represent the surfaces of a DNA chip on which DNA probes are immobilized, a DNA chip after hybridizing target DNA with the probes on the chip, and a DNA chip after treating nuclease onto the chip, respectively. And, the nucleic acid probe includes DNA, RNA or PNA (peptide nucleic acid); the nuclease includes exonuclease and endonuclease, which digests single strand nucleic acid independently or mixture thereofs, whose example are exonuclease I, S1 nuclease, mung bean nuclease, ribonuclease A, ribonuclease T1 and nuclease P1.

The invented method is applicable to all of the detection methods that distinguish effectively single strand from double strand nucleic acids by hybridization, such as a method for detecting the difference of fluorescence signal, electrochemical signal, mass, electric charge, or optical signal.

The present invention is further illustrated in the following examples, which should not be taken to limit the scope of the invention.

EXAMPLE 1

Removal of Single Strand DNA Probe by Treatment of Exonuclease I Before Hybridization

Example 1-1

Immobilization of Probes

Oligomers (15mer, 100 pmoles/$\mu$l) with the amine-substituted 5'-terminus or 3'-terminus were immobilized on a slide glass coated with aldehyde group (SuperAldehyde substrates, TeleChem International Inc., U.S.A.) by spotting each 0.5 $\mu$l of oligomers by the aid of a pipette. After spotting, the slide glass was dried for 12 hours, washed off at 25° C. to remove probes not attached onto the surface of glass and residual spotting solution, and then dried again. The slide glass was washed twice with 0.2% (w/v) sodium dodecyl sulfate (SDS) for 5 minutes, twice with 95° C. distilled water for 5 minutes, twice with 25° C. sodium borohydride for 5 minutes, three times with 0.2% (w/v) sodium dodecyl sulfate (SDS) for 1 minute and twice with 25° C. distilled water for 1 minute. Then, the immobilized oligomer probe was labeled with FITC (fluorescein-5-isothiocyanate).

Example 1-2

Enzyme Reaction of Exonuclease I

Ten units of exonuclease I in 20 $\mu$l buffer solution was treated on a slide glass containing immobilized probes which were prepared by the same method as in Example 1-1, and the slide glass was incubated at 37° C. for 1–2 hours.

Example 1-3

Image Analysis

The fluorescent signal was analyzed by using Scanarray 5000 (GSI Lumonics, U.S.A.).

Figure 2:
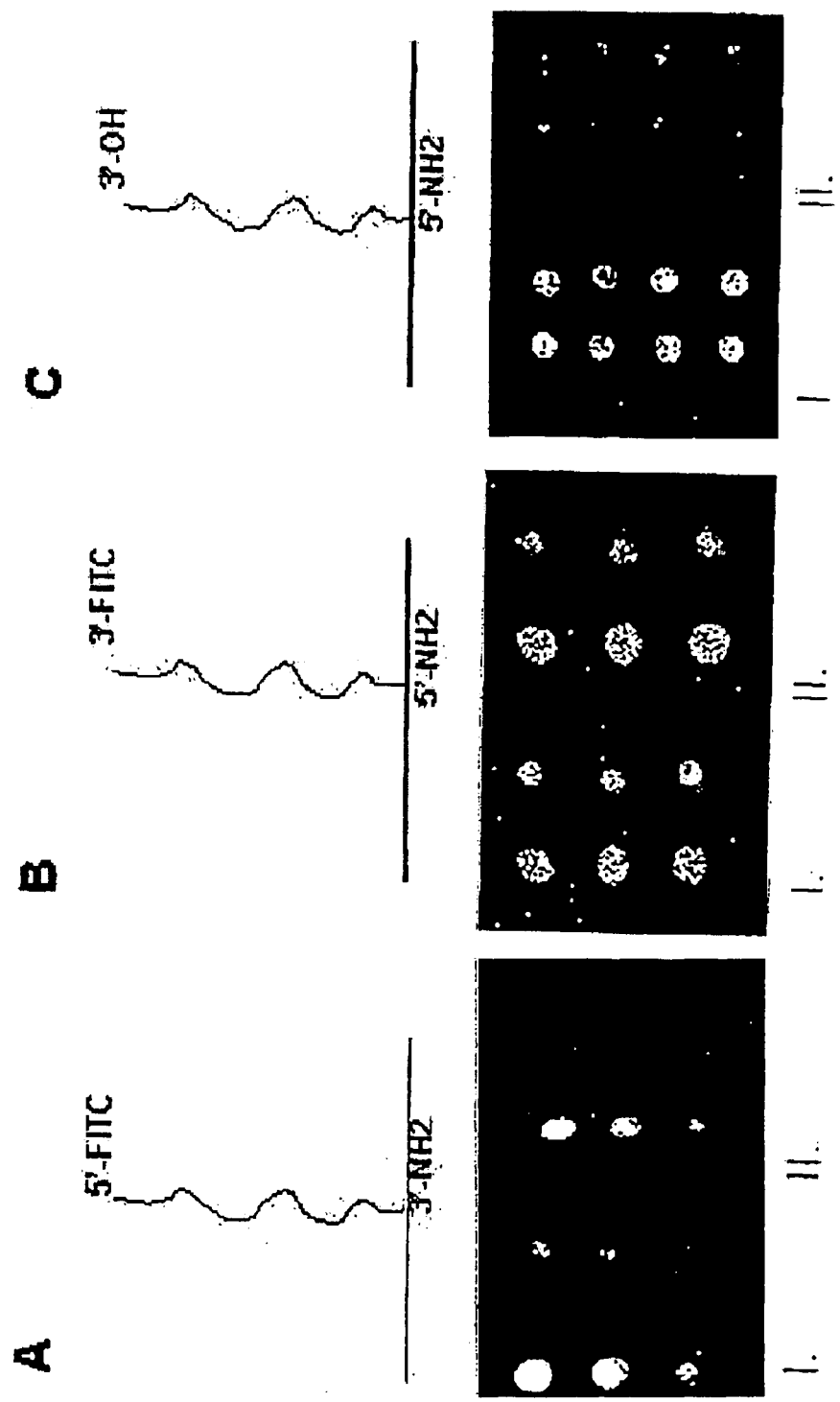
FIG. 2 is a photograph of fluorescent image showing the surface of a DNA chip, on which FITC-labeled target DNA is hybridized with the probes after treatment of exonuclease I.

FIG. 2 is a photograph of fluorescent image showing the surface of a DNA chip, on which FITC-labeled target DNA was hybridized with probes after exonuclease I treatment.

In FIG. 2, (A), (B) and (C) illustrate the surface of chip containing the probes of which 3'-terminus is immobilized on the surface and 5'-terminus is labeled with FITC, a chip containing the probes of which 5'-terminus is immobilized on the surface and 3'-terminus is labeled with fluorescence probes and a chip containing the probes of which 5'-terminus is immobilized on the surface and 3'-terminus is unlabeled hydroxyl group, respectively. In (A) and (B), (I) is a photograph of fluorescent image showing the surface of a DNA chip before exonuclease I treatment, and (II) is a photograph of fluorescent image showing the surface of a DNA chip after exonuclease I treatment. In (C), (I) is a photograph of fluorescent image showing the surface of a DNA chip of which probes are hybridized with the FITC labeled target DNA probes without exonuclease I treatment, and (II) is a photograph of fluorescent image showing the surface of a DNA chip of which probes are hybridized with the FITC labeled target DNA probes after exonuclease I treatment. As can be seen in FIG. 2, in both cases using probes whose 3'-terminus is immobilized on the surface as in (A) or using probes whose 3'-terminus is labeled with a fluorescent material as in (B), the fluorescent image does not show any difference, because exonuclease I does not react properly. On the other hand, in the case of using probes whose 3'-terminus is unlabeled hydroxyl group as in (C), the fluorescent image shows great difference in the presence and the absence of exonuclease I treatment, because the enzyme digests probes effectively.

This result is coincident with the character of exonuclease I, which hydrolyzes single strand DNA in a 3' to 5'-direction, and recognizes only 3'-terminus of single strand DNA with no recognition for the end of double strand DNA, more specifically 3'-terminus with a hydroxyl group.

EXAMPLE 2

Removal of Single Strand DNA by Exonuclease I Treatment After Hybridization of Target DNA

Example 2-1

Immobilization of the Probes

DNA oligomer was immobilized in a similar fashion as in Example 1-1.

Example 2-2

Hybridization of Target DNA

Ten microliters of FITC labeled target DNA (15 mer, perfectly matched oligonucleotides) in hybridization solution (UniHybTM Hybridization Solution, TeleChem International, Inc., USA) was added on a slide glass containing immobilized probes which were prepared by the same method as in Example 1-1, and the slide glass was incubated with a cover glass at 37° C. for 2–4 hours.

Example 2-3

Enzyme Reaction of Exonuclease I

Enzyme reaction was performed on a slide glass, on which DNA probes were hybridized by the same method as in Example 2-2, in a similar manner as in Example 1-2.

Example 2-4

Image Analysis

The fluorescent image was analyzed by the same method as in Example 1-3.

Figure 3:
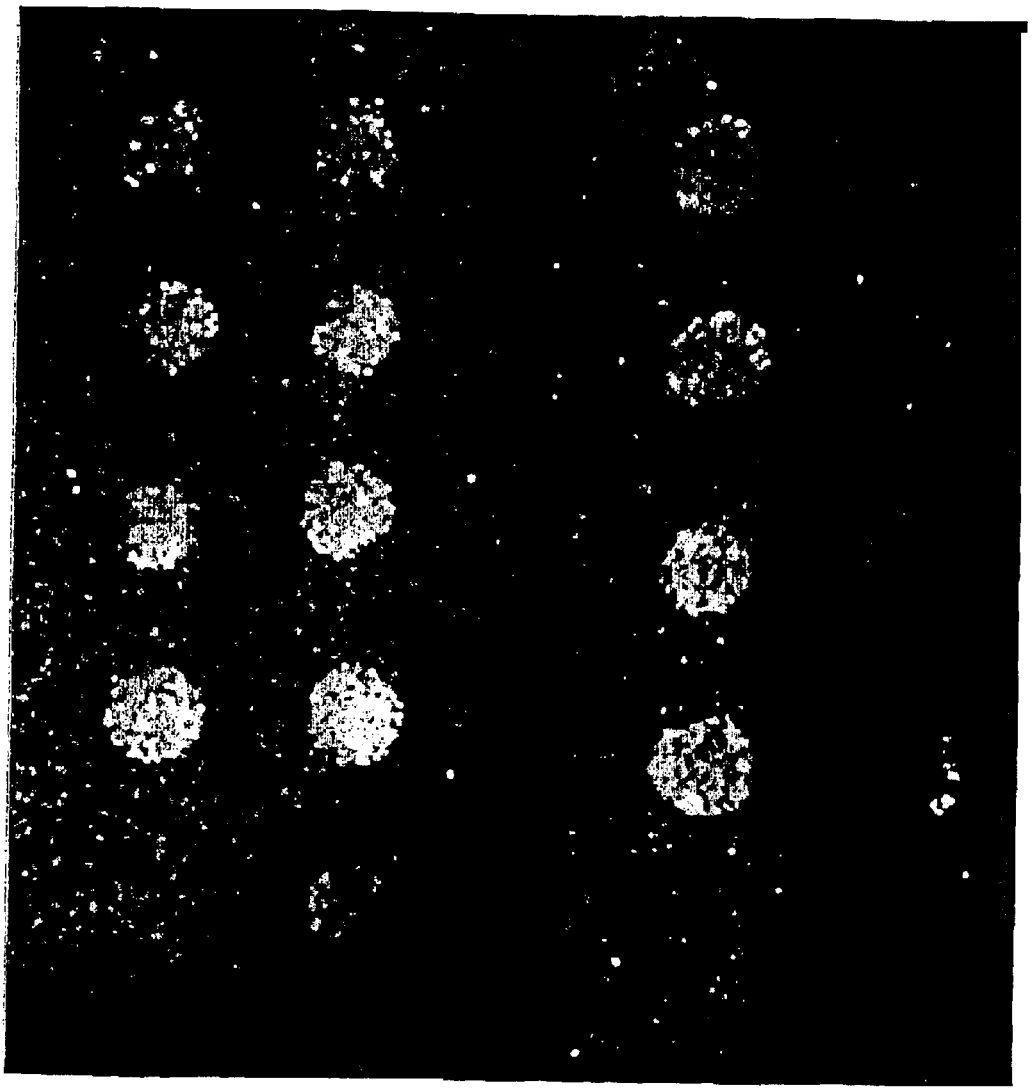
FIG. 3 is a photograph of fluorescent image showing the surface of a DNA chip, on which exonuclease I is treated after hybridization of FITC-labeled target DNA with the probes.

FIG. 3 is a photograph of fluorescent image showing the surface of a DNA chip on which exonuclease I was treated after hybridization of FITC labeled target DNA with probes on the chip. In FIG. 3, (I) and (II) show the surfaces of a DNA chip of which probes were hybridized with the FITC labeled target DNA in the absence of exonuclease I treatment, and a DNA chip of which probes were hybridized with the FITC labeled target DNA and treated with exonuclease I, respectively.

As shown in FIG. 3, exonuclease I treatment after DNA hybridization resulted in a little decrease of the fluorescent signal. Also, it seemed that the non-specific background signal was removed, because the control spot (the $5^{th}$ spot from the top) was removed almost perfectly after exonuclease I treatment.

EXAMPLE 3

Quantitative Analysis of the Removal of Single Strand DNA Probe Using Exonuclease I Treatment After Hybridization

Example 3-1

Immobilization of the Probes

One hundred nanomoles of 35mer oligomer DNA was immobilized on a chip containing streptavidin as a surface reactor at a flow rate of 10 µl/min for 5 min. Then, the chip was washed twice with 50 mM NaOH solution containing 1M NaCl for 1 minute. Biotin is attached to the terminus of the oligomer DNA probe.

Figure 4:
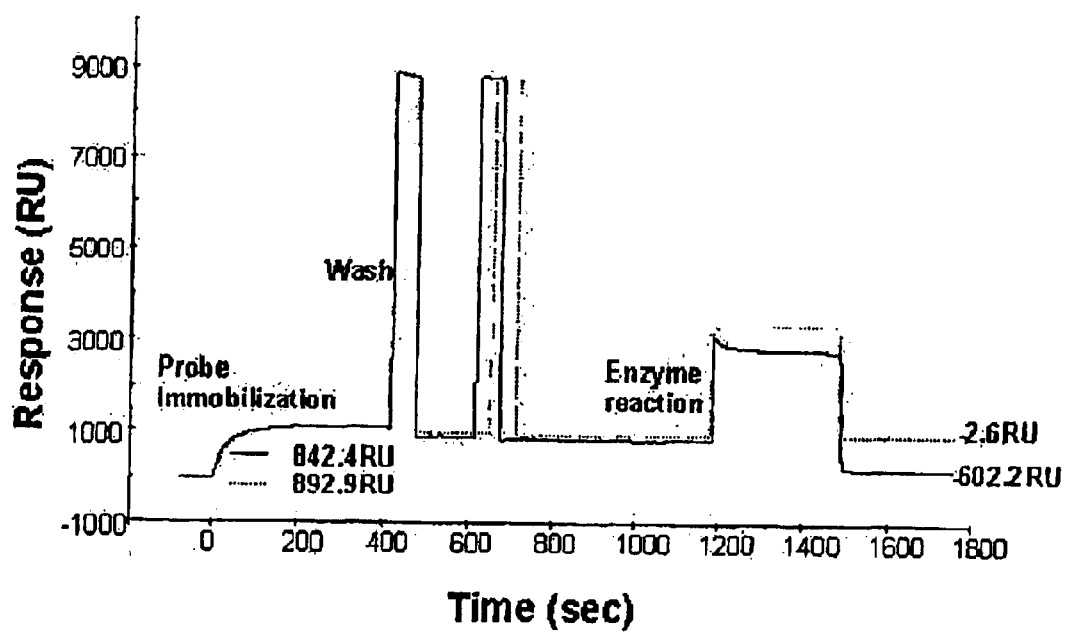
FIG. 4 is a graph showing the changes in quantity of immobilized probes on a DNA chip via BIAcore assay.

The said process was analyzed via SPR (Surface Plasmon Resonance) 3000 system (BIACore) (see: FIG. 4). In FIG. 4, the solid line indicates the probes whose 5'-terminus is immobilized on the surface of a chip and 3'-terminus has a hydroxyl group, and the dotted line indicates the probes whose 3'-terminus is immobilized on the surface of a chip and 5'-terminus has a hydroxyl group.

As shown in FIG. 4, in the case of using the 5'-terminus immobilized probes, the change of resonance signal was 842.4RU and in the case of using the 3'-terminus immobilized probes, the change of resonance signal was 892.9RU. Considering that 1RU change is equivalent to 1 $pg/mm^2$, the quantity of both immobilized probes seems almost the same.

Example 3-2

Enzyme Reaction of Exonuclease I

One unit per microliter of exonuclease I was treated on a chip of which probes were immobilized by the same method as in Example 3-1 at a flow rate of 10 µl/min for 5 minutes, and the SPR analysis was followed.

As shown in FIG. 4, in the case of using the 5'-terminus immobilized probes, the resonance signal was decreased by 602.2RU (the solid line), but in the case of using the 3'-terminus immobilized probe, the resonance signal has little difference (the dotted line). From these results, it was demonstrated that exonuclease I recognizes and hydrolyzes only 3'-terminal hydroxyl group of single strand DNA.

As clearly illustrated and demonstrated as above, the present invention provides a method for improving detection sensitivity for hybridized nucleic acid which is immobilized on a solid support of sensing device for genetic analysis, by removing non-hybridized nucleic acid probe from the solid support with the aid of nuclease. In accordance with the invented method, background signal caused by single stranded probe that is not hybridized with target nucleic acid or signal caused by non-specific binding of target nucleic acid to probe is decreased or removed, which improves detection sensitivity for hybridization with a high accuracy, and minimizes the loss of hybridized nucleic acid in the course of washing background signal removed in the conventional method.

What is claimed is:

1. A method for improving detection sensitivity for hybridized nucleic acid immobilized on a solid support of a sensing device for genetic analysis, which comprises the steps of (i) hybridizing target oligonucleotides with nucleic acid probes whose 5'-termini are immobilized on the solid support and whose 3'-termini are unlabeled hydroxyl groups and (ii) removing non-hybridized nucleic acid probes from the solid support with the aid of an exonuclease that only recognizes a 3'-terminal hydroxy group of a single-stranded nucleic acids.

2. The method for improving detection sensitivity of hybridized nucleic acid of claim 1, wherein the solid support of a sensing device for genetic analysis is glass, quartz, silicon or plastic.

3. The method for improving detection sensitivity of hybridized nucleic acid of claim 1, wherein the sensing device for genetic analysis is a chip on which nucleic acids are immobilized.

4. The method for improving detection sensitivity of hybridized nucleic acid of claim 1 or claim 3, wherein the nucleic acid is DNA, RNA or PNA (peptide nucleic acid).

5. The method for improving detection sensitivity of hybridized nucleic acid of claim 1, wherein the exonuclease is exonuclease.

6. The method for improving detection sensitivity of hybridized nucleic acid of claim 1, wherein the hybridized nucleic acid is detected by the difference of fluorescence, electrochemical signal, mass, electric charge or optical signal.

* * * * *

UNITED STATES PATENT AND TRADEMARK OFFICE
CERTIFICATE OF CORRECTION

PATENT NO. : 6,905,829 B2 Page 1 of 1
APPLICATION NO. : 10/311939
DATED : June 14, 2005
INVENTOR(S) : Yoon K. Cho et al.

It is certified that error appears in the above-identified patent and that said Letters Patent is hereby corrected as shown below:

On The Title Page:
After item 62, insert --item (30) Foreign Application Priority
KR  10-2001-0020573 - 04/17/2001 --.

Signed and Sealed this

Twenty-eighth Day of November, 2006

JON W. DUDAS
*Director of the United States Patent and Trademark Office*